United States Patent
Souissi et al.

(10) Patent No.: US 11,315,678 B2
(45) Date of Patent: Apr. 26, 2022

(54) METHOD AND APPARATUS FOR AN INTELLIGENT SCHEDULE BOARD FOR OPERATING ROOMS FOR SURGICAL CENTERS AND HOSPITALS

(71) Applicants: Slim Souissi, San Diego, CA (US);
Binu Johnson, San Diego, CA (US);
Mehdi Souissi, San Diego, CA (US)

(72) Inventors: Slim Souissi, San Diego, CA (US);
Binu Johnson, San Diego, CA (US);
Mehdi Souissi, San Diego, CA (US)

(73) Assignee: Ospitek, Inc., San Diego, CA (US)

( * ) Notice: Subject to any disclaimer, the term of this patent is extended or adjusted under 35 U.S.C. 154(b) by 0 days.

(21) Appl. No.: 16/929,286

(22) Filed: Jul. 15, 2020

(65) Prior Publication Data
US 2022/0020476 A1    Jan. 20, 2022

(51) Int. Cl.
*G16H 40/20*       (2018.01)
*G16H 40/00*       (2018.01)
*H04W 4/33*        (2018.01)
*H04W 4/029*       (2018.01)

(52) U.S. Cl.
CPC ............. *G16H 40/20* (2018.01); *G16H 40/00* (2018.01); *H04W 4/029* (2018.02); *H04W 4/33* (2018.02)

(58) Field of Classification Search
CPC ........ G16H 40/00; G16H 40/20; A61B 34/00; A61B 34/10; A61B 34/101; A61B 34/107; A61B 34/25; A61B 34/252; A61B 34/254; A61B 5/00; A61B 5/002; A61B 5/11; A61B 5/1113; A61B 5/742; G06Q 10/00; G06Q 50/00; G06Q 50/22; G06F 19/00; G06F 17/00; H04L 29/00; H04L 29/06; H04L 29/08
See application file for complete search history.

(56) References Cited

U.S. PATENT DOCUMENTS

| | | | | |
|---|---|---|---|---|
| 2010/0198609 A1* | 8/2010 | Mellin | ................... | G06Q 10/00 705/2 |
| 2012/0136671 A1* | 5/2012 | Alt | ......................... | G16H 40/20 705/2 |

(Continued)

OTHER PUBLICATIONS

NPL_search (Sep. 8, 2021).*

*Primary Examiner* — Van T Trieu
(74) *Attorney, Agent, or Firm* — Pablo Meles (57) ABSTRACT

A method for providing an intelligent schedule board for operating rooms in surgical centers and hospitals is provided. The method comprises displaying an estimated location of a patient on an operating room schedule board and displaying status information on the operating room schedule board. The method also comprises automatically updating the schedule dashboard as at least one of the location and the status of the patient changes. Patient location is estimated using an indoor tracking system and wherein the system is an RTLS system. Patient status information is entered by staff members by means of at least one of a tablet device, a phone device, and a computer. Patient status information is entered automatically by means of a computer vision scheme that detects patient status comprising at least one of a start of surgery and an end of surgery. Patient status information is entered using a voice recognition scheme.

20 Claims, 5 Drawing Sheets

(56) References Cited

U.S. PATENT DOCUMENTS

| | | | | |
|---|---|---|---|---|
| 2014/0006943 A1* | 1/2014 | Robbins | ............... | H04L 67/025 |
| | | | | 715/273 |
| 2014/0278522 A1* | 9/2014 | Ramsey | ............... | G16H 10/60 |
| | | | | 705/3 |
| 2015/0317440 A1* | 11/2015 | Brock-Utne | ........... | G16H 40/20 |
| | | | | 705/2 |
| 2016/0323417 A1* | 11/2016 | Spear | ..................... | H04L 67/36 |
| 2017/0061375 A1* | 3/2017 | Laster | ................. | G06Q 10/087 |
| 2021/0386326 A1* | 12/2021 | Souissi | ............... | A61B 5/1113 |

* cited by examiner

METHOD AND APPARATUS FOR AN INTELLIGENT SCHEDULE BOARD FOR OPERATING ROOMS FOR SURGICAL CENTERS AND HOSPITALS

FIELD OF THE INVENTION

The present disclosure in the field of health care patient management. More particularly, the present disclosure provides systems and methods of tracking and reporting patient location and status before, during, and after surgical procedures and dynamically making scheduling and other changes based on various events.

BACKGROUND AND PROBLEMS ADDRESSED HEREIN

Operating room management in a hospital or surgical center requires co-ordination between surgeons, anesthesiologists, nurses, technicians, and other support staff. Efficient management of special equipment and visibility into the availability of this equipment and the operating rooms is also important.

To facilitate coordination, surgical centers and hospitals create schedules for operating rooms. Schedules may be manually recorded on a large white schedule board or projected onto a large TV screen. The schedule board may display surgical procedures planned for the day.

For each procedure, a typical schedule board displays the designated operating room, patient name, age, gender, procedure start time, and procedure name. Medical staff assigned to the procedure and any special equipment needed for the procedure are also shown.

Operating room schedules are usually published before the start of the day or at the end of the prior day. Medical staff refer to this schedule to determine which operating rooms they should be in at what time and for what surgery.

Support staff who move special equipment refer to this schedule to determine when and where to deliver special equipment for surgical procedures. Cleaning crews refer to the schedule to plan their work during operating room turnover. Administrative staff may also refer to the schedule to keep patient family members updated about their loved ones.

As the day progresses, events may occur that necessitate changes to the schedule. A surgeon or patient may be delayed or surgery may be cancelled for various reasons. Delay, cancellation or other changes to a procedure could change the start time of subsequent procedures. Changes could also affect the operating room in which the subject procedure had been planned. Medical staff assigned to the changed procedure may get reshuffled and special equipment may need to be relocated to different operating rooms or reprioritized.

Hospitals and surgical centers use operating room coordinators/managers to detect and respond to events that necessitate changes to schedule. Operating room co-ordination staff manages operations of the surgical center and make necessary changes to schedules and communicates such changes to staff involved.

A comprehensive solution to operating room scheduling for hospitals and surgical centers is needed to address problems arising from unexpected events that are disruptive to a schedule. Detecting the need for a schedule change requires coordination and communication. An operating room scheduler needs to determine, for instance, if a patient has not checked in on time, if a patient is getting delayed in pre-op, or if the surgeon was late coming to the surgical center.

A need exists for reducing or eliminating the need for manual coordination work between different staff members. Such manual coordination may require meetings, phone calls emails, or texting. Other disruptive events could be the absence or unavailability of special equipment necessary for the planned surgery, the cancellation of a surgery, or a last-minute addition of a non-scheduled procedure.

An additional problem is errors and inefficiencies associated with manual updating of static white board schedules based on unpredicted and disruptive changes. Manually changing schedules is labor intensive and prone to human error. Systems and methods provided herein reduce or eliminate the need for such manual steps by automatically implementing schedule changes based on scheduling constraints that relate to patient, procedures, staff and equipment. The need must be reduced for manual updates to white boards with new schedules and to physically locate medical staff, nurses and surgeons who could be in different operating rooms to advise them of changes in their schedules.

A further problem is determining patient location and status within a hospital or surgical center. Many questions must be answered: Did the patient arrive? Is the patient already at the PreOp getting prepared for surgery? Did the anesthesiologist evaluate health history of the patient and approved surgery? Did the surgeon examine the patient and approve the surgery? Did the PreOp nurse perform all the necessary medical work and complete the necessary paperwork to move the patient to the operating room? Finding out about patient location and status is sometimes difficult and involves either talking to multiple staff members, and consulting paperwork and electronic records.

Finally, scheduled durations of surgical procedures are static but cause disruption when surgery exceeds allocated procedure time. Running multiple operating rooms simultaneously is complicated, particularly when the durations of surgeries are not accurately estimated. Such incorrect estimation may result in conservative scheduling which is inefficient and plagued with long waiting time for patients. Incorrect estimation also forces operating room coordinators to constantly monitor multiple operating rooms for surgery status and manually update the schedule based on staff availability, equipment availability and operating room availability.

The problems addressed herein are caused by inefficient and error-prone coordination between staff members, doctors, nurses, patients, medical staff members. Problems are further associated with equipment availability issues leading to extended patient wait times, underutilization of equipment and overstaffing in number of personnel and number of working hours. Each of these issues has direct correlation to patient satisfaction and safety.

Prior art includes manual white board for surgical scheduling. Prior art also includes electronic operating room dashboards that are manually entered to visualize operating room schedule on a TV screen. This solution may be offered by a vendor named Casetabs Inc. Electronic operating room dashboards are also sold by EPIC and Cerner systems.

Surgical centers and hospitals therefore need a comprehensive solution that allows managing operating room schedules dynamically and intelligently.

SUMMARY

Figure 1:
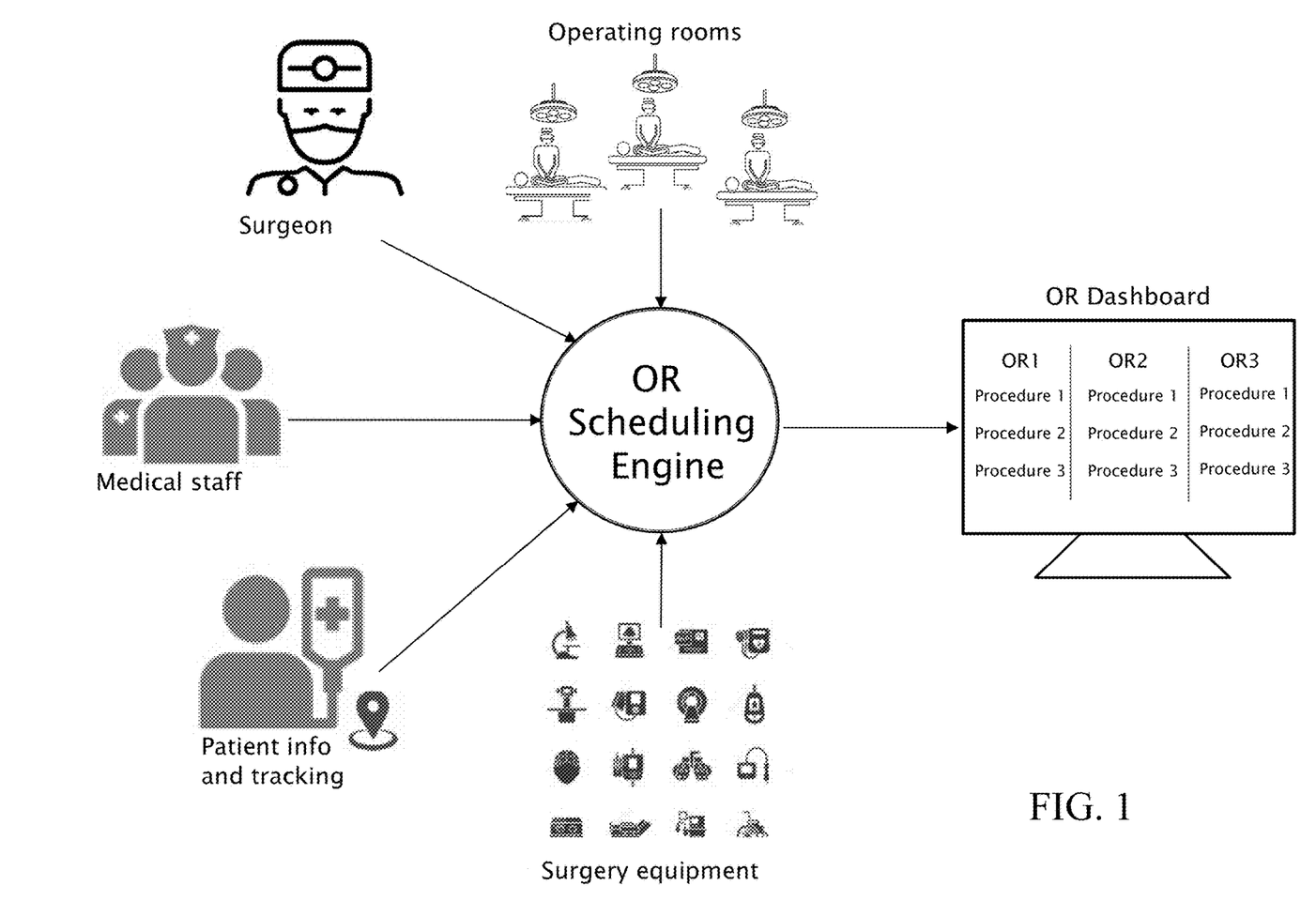
FIG. 1 is a diagram of how information is fed into an operating room scheduling engine to create schedule.

Systems and methods provided herein for an intelligent schedule board for operating rooms in surgical centers and hospitals are based on three major subsystems. The subsystems are illustrated in FIG. 1 which shows input information that feeds into a scheduling engine. The information includes patient information including name, age, gender, location, time spent in waiting room, time spent in Preop, and time spent in operating room. The information also includes surgery status, surgeon name, anesthesiologist name, type of anesthesia, equipment needed, availability of needed equipment, staff members, and which operating room is used for which surgery.

Figure 2:
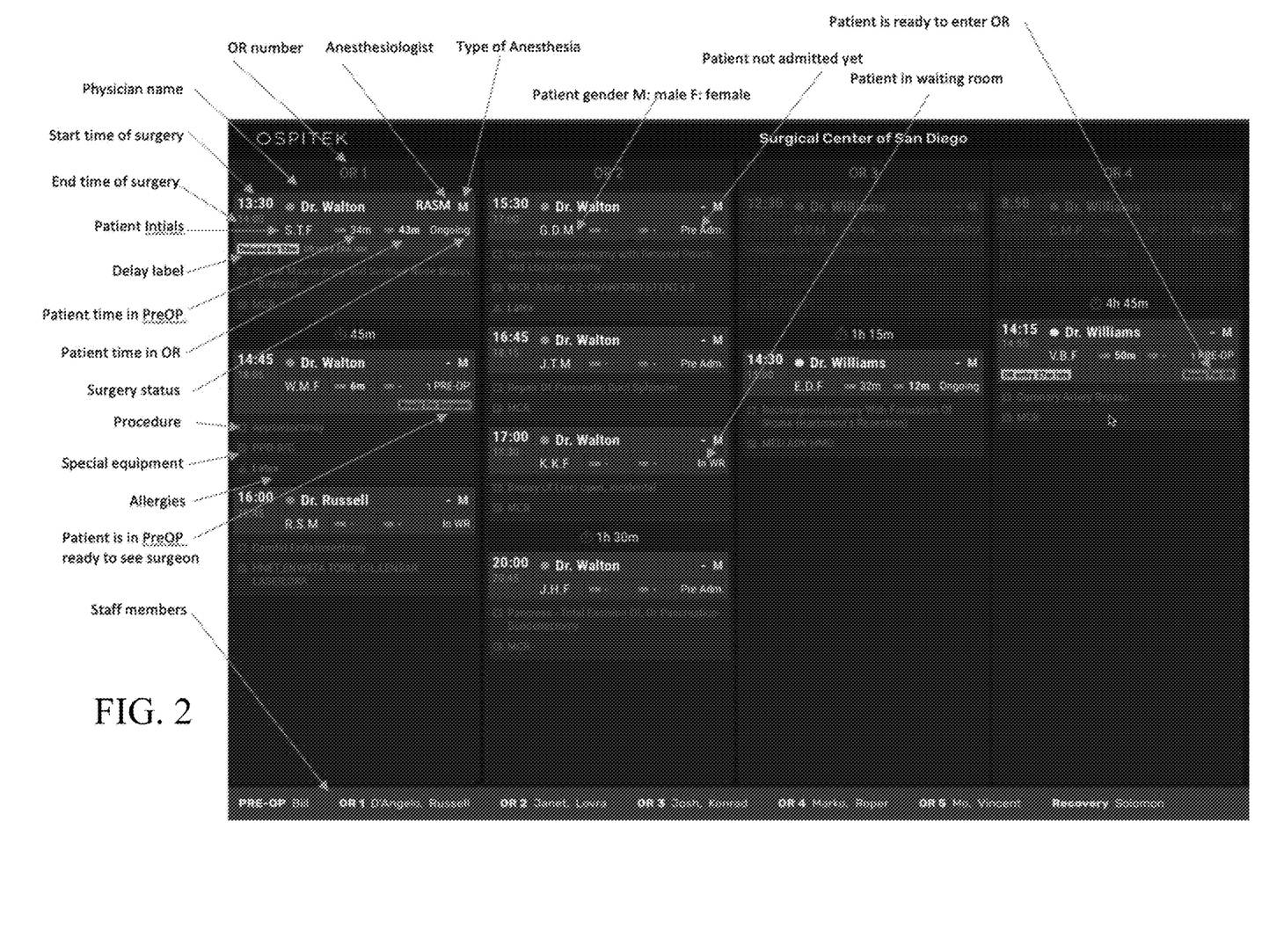
FIG. 2 illustrates an operating room dashboard with a visualization of procedure data along with patient status as provided by a tracking system and status updates according to an embodiment of the present disclosure.

A first subsystem is a visualization engine that renders a simple and intuitive illustration of a procedure involving information about patient name, age, gender, physician name, anesthesiologist, type of anesthesia, type of allergies, type of surgery, medical staff supporting the surgery, equipment needed for the surgery and other parameters relative to the procedure. The visualization engine drives a display (television or computer monitor) to show a table view of operating rooms and scheduled procedures as illustrated in FIG. 2. FIG. 2 illustrates a preferred embodiment of the OR dashboard with a visualization of procedure data along with patient status as provided by the tracking system and the status update via tablets and computers.

The visualization engine provides staff members with a simple and intuitive view of the status of scheduled surgeries during a given day. By viewing the display, a staff member sees what surgeries have been completed, which surgeries are underway and at what stage, and the upcoming surgeries scheduled for specific operating rooms. Briefly viewing a display provides a comprehensive view of the entire surgical operations.

A second subsystem is a tracking engine for tracking patient location and patient status within the surgery center. Patient location and status are automatically communicated to the visualization engine allowing the status of the procedure to be updated live as the patient moves around the surgical centers and goes through the surgery steps. By synchronizing the tracking engine with the visualization engine, it can be shown on the operating room schedule that the patient has arrived to the surgery center and how long he/she stayed at the waiting room or at the PreOp.

The system also illustrates with labels when the patient is ready for surgeon or ready to move to the operating room. Patient status information may be entered via a tablet device. For example, a patient may be ready to see the surgeon or a patient may be ready to enter the operating room. The time spent by the patient in the waiting room, in the PreOP, or in the operating room is calculated automatically by the tracking engine.

A third subsystem is a predictive and optimization engine that estimates the expected procedure duration based on a learning function. The engine uses status of surgery, patient information, surgery information, surgeon information and history of similar surgeries to estimate the duration of the surgery.

The engine notifies staff about delays and potential conflicts between scheduled surgeries. The engine proposes means to reschedule surgeries to optimize the overall surgical center operation. For example, when a surgery is underway, the engine allows for estimating the expected completion time of surgery thus allowing the operating room coordinator to plan usage of the operating room.

The engine also allows nurses in the recovery room to obtain information about status of patients in operating room and when they are expected to be moved to the recovery room. This may assist the nursing staff to plan their workload as they monitor the status of surgeries on a live basis. This information is also useful to cleaning crews in planning their activities according to expected operating room turnover.

The present disclosure utilizes inputs from a patient locating/tracking system and status to automatically visualize patient location on the operating room dashboard and estimate patient readiness for surgery. It also uses a learning function and analyses a large number of procedures to estimate the duration of a given procedure based on past history. Such estimation may involve learning from data such as the identity of the surgeon performing the surgery, the type of surgery, the type of equipment used, and patient age and health conditions.

During surgery and based on the status of the procedure, the learning function estimates a completion time of procedure and the time the patient will be moved out of the operating room.

The present disclosure also connects inputs from pre-op nurse station to operating room scheduling system to automatically detect delays in patient readiness or procedure cancellation. Information such as patient being readiness for surgery or readiness to see the surgeon is entered by the PreOp nurse on a tablet device, automatically captured by a server, and displayed on the TV screen.

Systems and methods provided herein also connect inputs from enrollment desk to operating room scheduling system to detect delays in patient check-ins or early arrivals of patients. Delays in ongoing procedures are detected that affect start time of subsequent procedures.

The detection of delayed procedure is either completed through a learning function from past procedures or by detecting that the patient is still in the operating room while the schedule shows that the procedure should be completed. The present disclosure further schedules new start times for procedures when it detects a delay and uses a new start time based on operating room availability, support staff availability, and constraints that relate to surgeon availability and special equipment availability.

Systems and methods also make automatic schedule changes when the system is run in autonomous mode. The system can change the start time of a procedure, the operating room for the procedure and the duration of the procedure.

The system can be run in supervised mode. The system sends proposed schedule changes to supervising staff as notifications and makes the changes only if approved by supervising staff.

The system automatically updates the operating room schedule board to reflect schedule changes during the day. This keeps the information presented on schedule board dependable. The updates are based on information fed from the patient tracking system, the equipment tracking system and the patient status updates entered by staff members from tablet device or computer.

Systems provided herein reduce or eliminate manual efforts in rescheduling and in keeping schedule board up to date. Patient status (e.g. checked-in, ready for surgery) is shown and is overlaid on the schedule board so surgeons, staff and coordinators have an enhanced view of the upcoming schedule.

Systems provided herein use machine learning to learn of and estimate duration by procedure types and by procedure type for per physician. Systems use this information to detect if subsequent procedures are at risk of getting delayed. By learning from thousands of procedures, the intelligent operating room scheduling engine can estimate the procedure duration based on patient information (age, gender, medical history), the surgeon performing the surgery and the surgeon's history performing similar procedures. When the procedure is progressing and as the procedure status is updated (time out, start procedure closing), the estimated time of surgery completion is refined. Based on changes to the surgery start time and end time, the optimization engine moves procedures around automatically and notifies staff on the monitor or via text messaging.

DETAILED DESCRIPTION

Systems and methods provided herein comprise a scheduling server and a schedule board, preferably a television screen or computer monitor. The scheduling server is a remote server that receives inputs from a patient enrollment desk, from nursing station terminals (e.g. computers, tablets), and from patient tracking system.

The inputs may be sent to the scheduling server via the Internet, via private network, or via other means. The scheduling server also receives status about equipment availability and its whereabouts within the center. Equipment location is sent by the tracking system. Special equipment needs and availability is established for each scheduled procedure.

Schedule board is run as an application that drives a large display like a TV screen. A preferred method is to run the schedule board as an application (or as a browser application) on a large smart TV. Schedule board gets up to date data from schedule server via the Internet and displays the schedule. This is illustrated by FIG. 2.

The scheduling server uses inputs to detect if a change in schedule is warranted. Common inputs that warrant a change in the schedule are patient delays, procedure cancellations, physician delays, equipment not available, patient health issues, and missing medical staff.

The scheduling server has knowledge of automatic schedule changes that it can make and schedule changes that do not require approval from an operating room coordinator. The system provides a user interface for administrators and operators to specify these rules.

The system makes schedule changes automatically when run in autonomous mode. When run in supervised mode, the system sends proposed changes to supervising staff (as notifications) and makes the changes as approved by supervising staff.

The system detects needs and opportunities for four types of changes. First, delay start time of a procedure. If a planned procedure is delayed, the system evaluates the need to delay the start time of subsequent procedures in the same operating room by the same surgeon and staff. If scheduling constraints are met, the system changes the start time of next procedure and applies the same test/action for subsequent procedures. For instance, if procedure 1 in operating room 1 has a 30 minute delay, then all procedures scheduled in operating room 1 may be automatically rescheduled with a 30 minute delay. The scheduling board dynamically changes the start time for each procedure to reflect the propagation of the delay caused by procedure 1.

Second, advance start time of a procedure. If a planned procedure is canceled or is completed sooner than expected, the system evaluates the opportunity to advance start time of subsequent procedures in the same operating room by the same surgeon and staff. The system uses patient enrollment time, entry time to pre-op, and status inputs from pre-op to make a preliminary determination of an opportunity to possibly advance start time of a procedure. If scheduling constraints are met, the system advances the time of the next procedure and applies the same test/action for subsequent procedures.

Third, move operating rooms for a procedure. Sometimes an operating room is assigned to a surgeon for a block of time (e.g. operating room 1 is assigned to a surgeon from 6 am to noon). When the system makes any changes to the time schedule or procedures, the system checks the operating room assignment constraints to detect conflicts based on operating room assignments. If such a conflict is detected, the system finds alternative operating rooms to move the procedure to. If the system is given the autonomy, the system would make this change automatically. Otherwise, system sends this change recommendation as part of the notification to appropriate personnel and makes the change on approval received from such personnel.

Fourth, change support staff for a procedure. Usually nurses and technicians are assigned to a group of surgeries by a surgeon or in an operating room. Once that group of procedures is complete, the personnel could be scheduled to switch to a different operating room/surgeon. For example, a nurse could be assigned the team for physician 1 in the morning and then to the team for physician 2 in the afternoon. When system makes any changes to the scheduled time of procedures, it evaluates if staff changes are required. Any changes to start time of a procedure or a move to a new operating room needs validation of staff availability and special equipment availability.

The system further includes a learning function to estimate procedure time. In a preferred embodiment, the system can estimate the duration of a procedure as it is underway in the operating room. For example, based on the start time of the procedure, which may be captured by an operating room nurse through an operating room tablet device, and looking into historical data for the same surgeon performing the procedure, for example a knee replacement for a healthy 50 year old patient, the system may use the average duration of the past 100 knee replacement surgeries for a same age and similar health patient to estimate the duration of the procedure. If the estimate shows that the procedure is expected to be on time, then no action is taken. If the procedure is estimated to be late then schedule changes may be warranted. More advanced estimation techniques may be used to determine patient exit time from the operating room. This involves examination of surgeon history performing same procedure, patient health history, patient age, equipment used in surgery, and staff supporting surgery.

Figure 3:
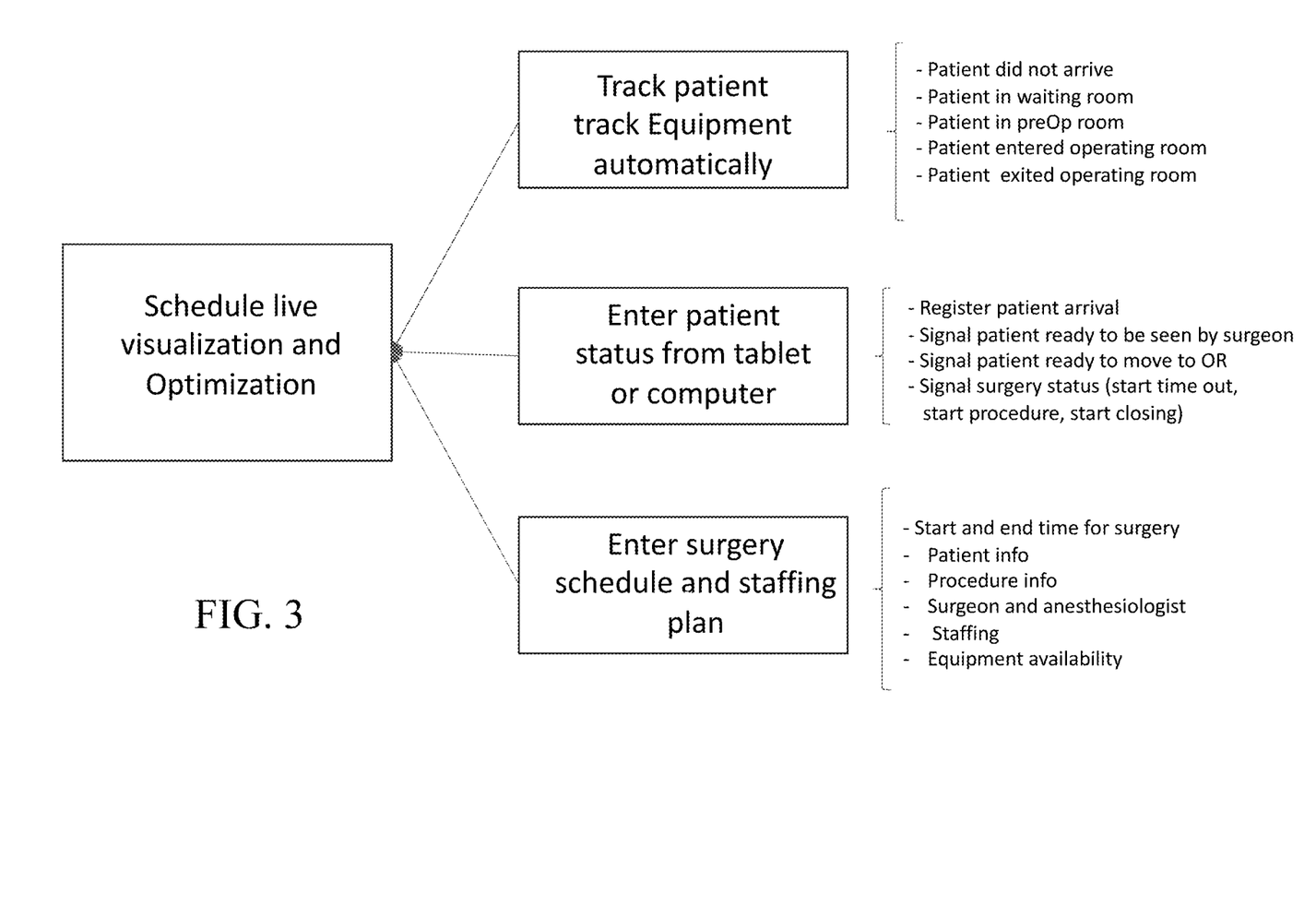
FIG. 3 is a diagram illustrating elements of scheduling live visualization and optimization according to an embodiment provided herein.

FIG. 3 is a diagram illustrating elements of scheduling live visualization and optimization according to an embodiment provided herein. The elements comprise the various steps toward moving a patient through the surgery process and outcomes of inquiries at each step.

Figure 4:
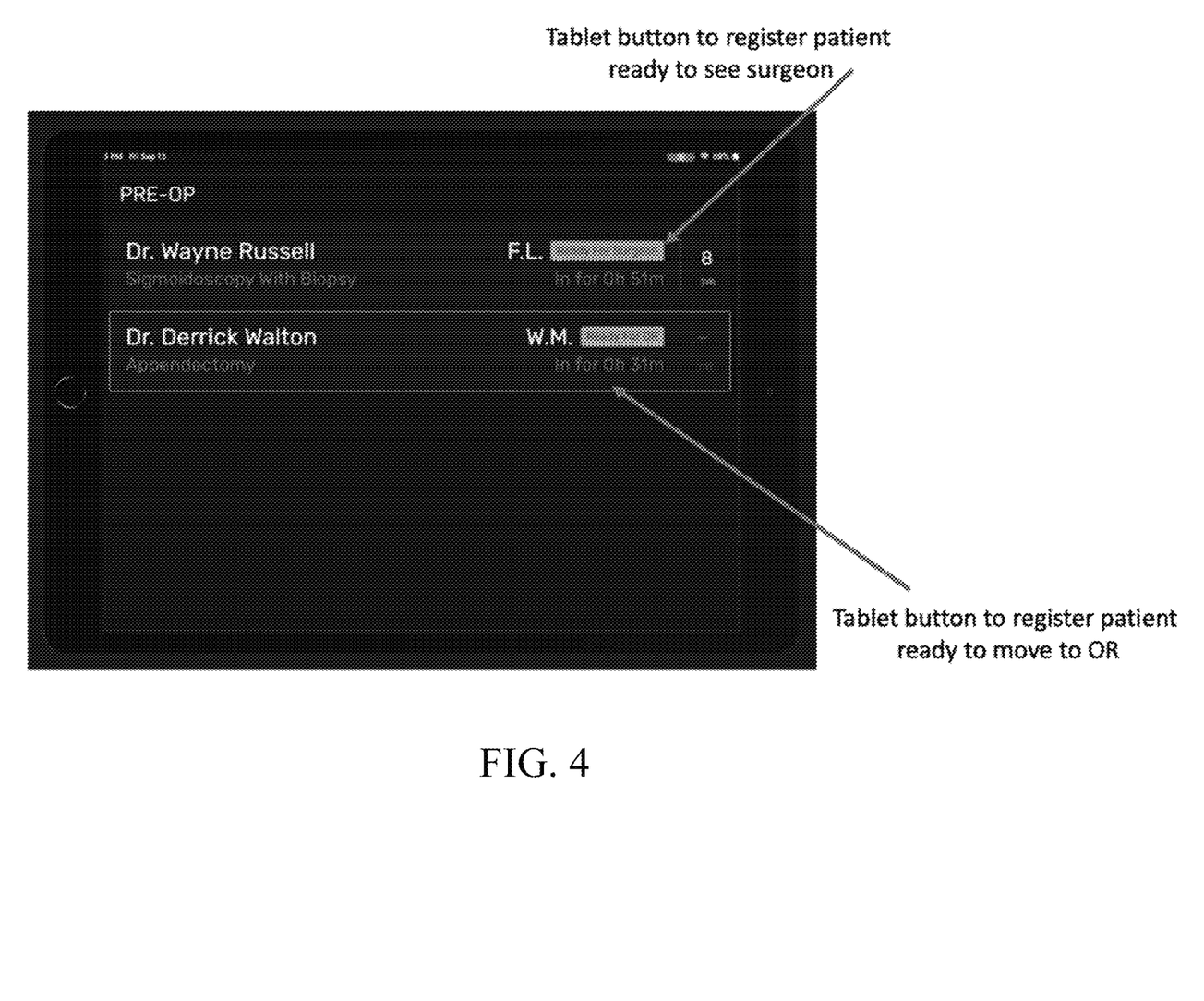
FIG. 4 is an illustration of a sample PreOP tablet device to signal patient status and readiness to move to an operating room.

FIG. 4 is an illustration of a PreOP tablet device to signal patient status and readiness to move to an operating room. A sample ProOP status is shown that an operating room administrator or other professional may view.

Figure 5:
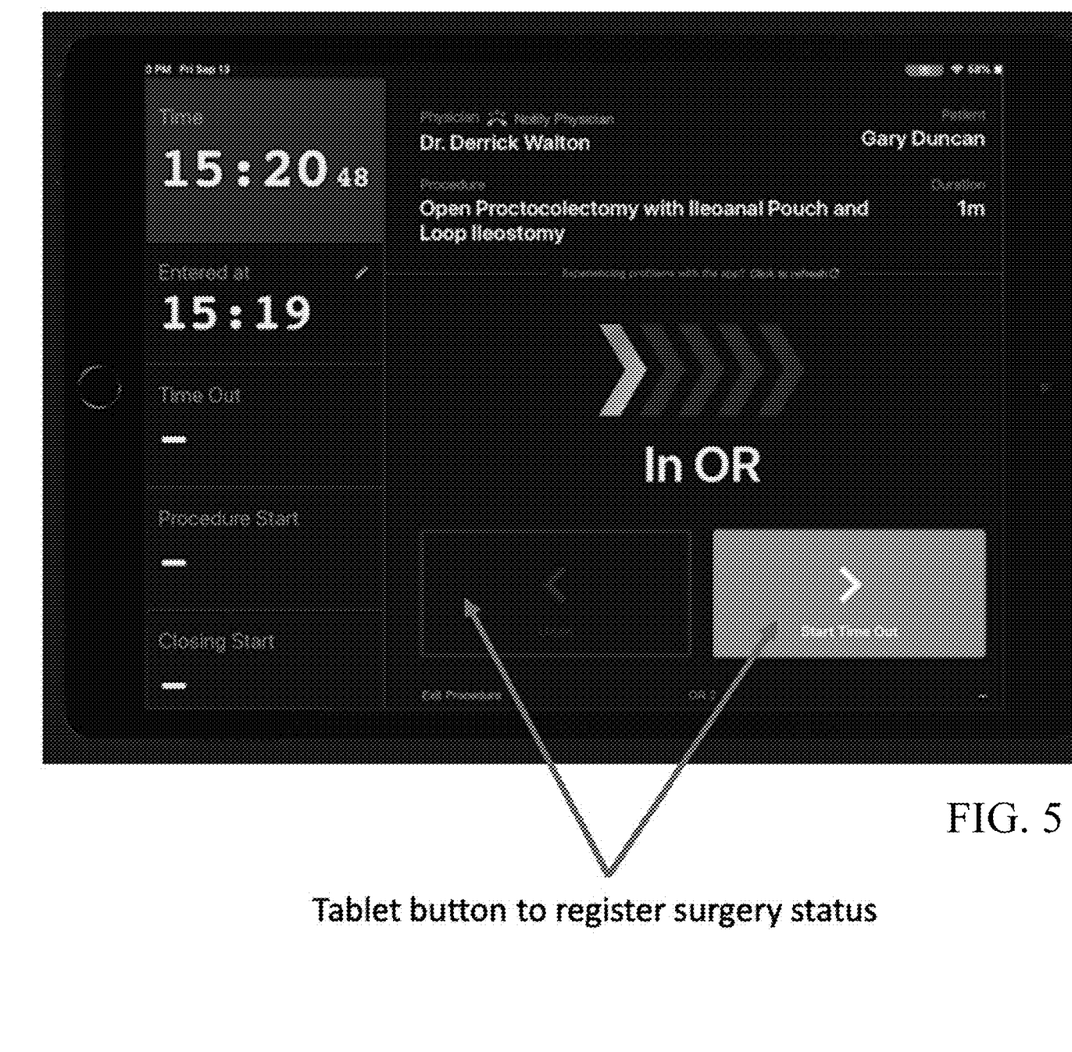
FIG. 5 is an illustration of a sample operating room tablet device to capture patient status during surgery.

FIG. 5 is an illustration of a sample view of an operating room tablet device to capture patient status during surgery. Patient and surgeon names, surgery description, and surgery start time are displayed.

What is claimed is:

1. A method for providing an intelligent schedule board for operating rooms in surgical centers and hospitals, comprising:
    tracking an estimated location of a patient including arrival to the surgical center or hospital and locations at a waiting room, a preoperative room, and operating room;
    tracking a patient status within the surgery center or hospital;
    displaying the estimated location of the patient on an operating room schedule board;
    displaying status information on the operating room schedule board; and
    automatically updating the schedule dashboard as the location and the status of the patient changes.

2. The method of claim 1, wherein the patient location is estimated using an indoor tracking system and wherein the system is a real time location system.

3. The method of claim 2, wherein the tracking system provides input about the time spent by the patient in a waiting room, in a preoperative room and in an operating room.

4. The method of claim 1, wherein the patient status information is entered by staff members by means of at least one of a tablet device, a phone device, and a computer.

5. The method of claim 1, wherein the patient status information is entered automatically by a computer vision scheme that detects patient status comprising a start of surgery and an end of surgery.

6. The method of claim 1, wherein the patient status information is entered by means of a voice recognition scheme.

7. The method of claim 1, wherein schedule changes are automatically updated on the schedule board.

8. The method of claim 7, wherein schedule changes involve moving a procedure from a first operating room to a second operating room.

9. The method of claim 7, wherein a server sends a notification to staff in an event a schedule is changed.

10. The method of claim 1, wherein a notification is sent to an operator prior to schedule changes and wherein the operator approves or rejects the proposed change.

11. A method for maintaining and updating an operating room schedule board, comprising:
    receiving information of a patient being tracked including an estimated location of a patient including arrival to the surgical center or hospital and locations at a waiting room, a preoperative room, and operating room;
    receiving information of a patient status within the surgery center or hospital;
    overlaying patient location and patient status information on an operating room schedule board;
    detecting changes to an operating room schedule; and
    automatically updating the board by rescheduling procedures based on the detected change.

12. The method of claim 11, wherein changes to the schedule are caused by at least one of patient delay, surgeon delay, cancelled procedure(s), lack of equipment, and lack of medical staff availability.

13. The method of claim 11, wherein schedule updating uses machine learning to estimate duration of procedures by procedure type and by a particular surgeon performing the surgery and a surgeon's history of performing similar procedures.

14. The method of claim 11, wherein a schedule server uses machine learning and artificial intelligence to learn and estimate durations of procedures, the durations based on factors comprising at least one of procedure type, physician, and patient age and wherein the machine learning estimates a completion time of procedure and the time the patient will be moved out of the operating room.

15. The method of claim 11, wherein a schedule operator specifies operating room change constraints.

16. A system for providing an intelligent schedule board for operating rooms in surgical centers and hospitals, comprising:
    a server; and
    one or more an applications executing on the server including a visualization engine, a tracking engine, and a predictive and optimization engine that:
        tracks patient location and patient status within the surgical center or hospital and updates the patient location and patient status live as the patient moves through surgery steps wherein the predictive and optimization engine estimates an expected procedure duration based on a learning function that uses a status of surgery, patient information, surgery information, surgeon information, and history of similar surgeries to estimate the expected procedure duration;
        displays an estimated location of a patient on an operating room schedule board,
        displays status information on the operating room schedule board, and automatically updates the schedule dashboard as at least one of the location and the status of the patient changes.

17. The system of claim 16, wherein server estimates the patient location using an indoor tracking system and wherein the indoor tracking system is an real time location system.

18. The system of claim 16, wherein the patient status information is entered by staff members by means of at least one of a tablet device, a phone device, and a computer and wherein the system makes schedule changes automatically when run in an autonomous mode and sends proposed changes to supervising staff when run in a supervised mode.

19. The system of claim 16, wherein the system utilizes inputs from a patient locating/tracking system to automatically visualize patient location on an operating room dashboard and estimate patient readiness for surgery and further uses a learning function that analyzes a large number of procedures to estimate a duration of a given procedure based on past history including an identity of the surgeon performing the surgery, a type of surgery, a type of equipment used, and patient age and health conditions.

20. The system of claim 16, wherein the system dynamically changes scheduling of procedures upon detection of a delay start time of a procedure, upon detection of an advance start time of a procedure, upon detection of moving of an operating room for a procedure, and upon detection of a change of support staff for a procedure wherein changes to start time of a procedure or a move to a new operating room needs validation of staff availability and special equipment availability.

* * * * *